United States Patent [19]

Gummere et al.

[11] Patent Number: 4,678,049

[45] Date of Patent: Jul. 7, 1987

[54] BLOOD COLLECTION BAG WEIGHT MONITOR

[75] Inventors: John B. Gummere; Stephen C. Minney, both of Tucson, Ariz.

[73] Assignee: Engineering & Research Associates, Tucson, Ariz.

[21] Appl. No.: 788,423

[22] Filed: Oct. 17, 1985

[51] Int. Cl.$^4$ .................. G01G 3/08; G01G 19/00; B65D 81/00

[52] U.S. Cl. .................. 177/229; 177/245; 128/771

[58] Field of Search .................. 177/229, 245; 128/771

[56] References Cited

U.S. PATENT DOCUMENTS

| | | | |
|---|---|---|---|
| 3,115,152 | 12/1963 | Goldberg et al. | 177/245 X |
| 4,027,735 | 6/1977 | Floyd | 177/229 X |
| 4,378,854 | 4/1983 | Rosen | 177/245 X |

Primary Examiner—George H. Miller, Jr.
Attorney, Agent, or Firm—Cahill, Sutton & Thomas

[57] ABSTRACT

A weight monitor includes a first part for attachment to a pedestal or other support member and a second part for suspending a blood collection bag to be filled by a flow of blood from a donor. A trough shaped spring interconnects the first and second parts and retains the second part in fixed positional relationship to the first part until the bending force imposed upon the spring by the filling blood collection bag exceeds a predetermined value at which point the spring flexes abruptly and the second part becomes positionally reoriented with respect to the first part. A clamp, associated with the fill tube of the blood collection bag, is actuated by the reorientation of the second part to terminate further flow of blood through the fill tube into the blood collection bag.

22 Claims, 10 Drawing Figures

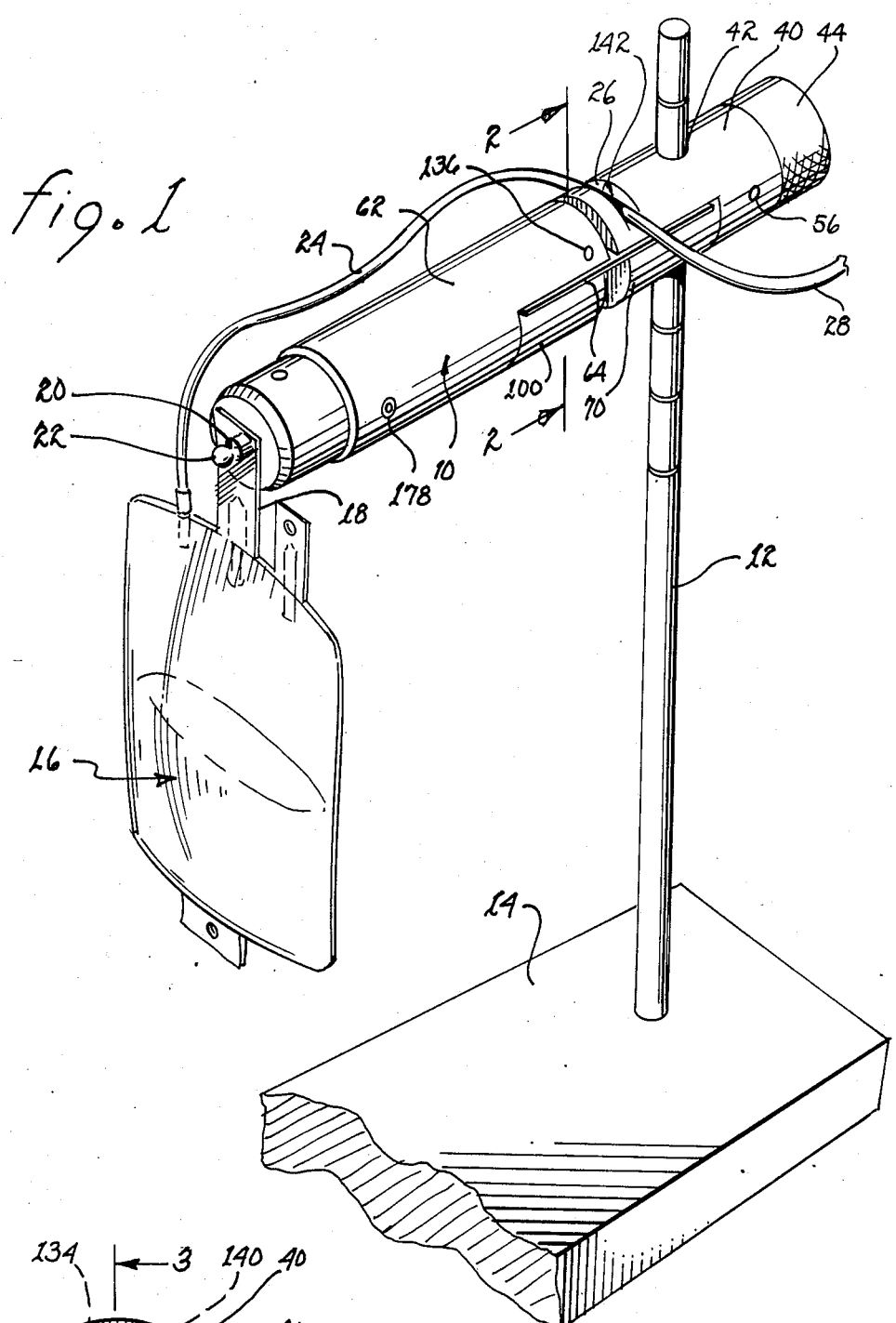

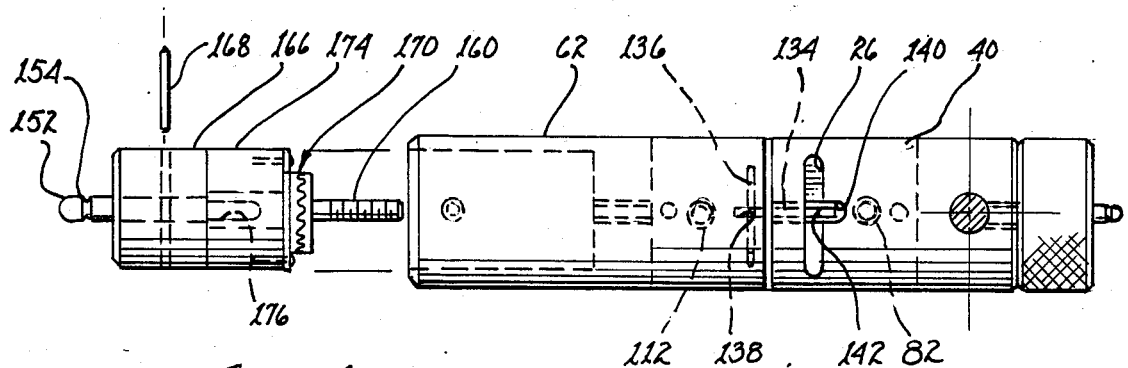
fig. 6
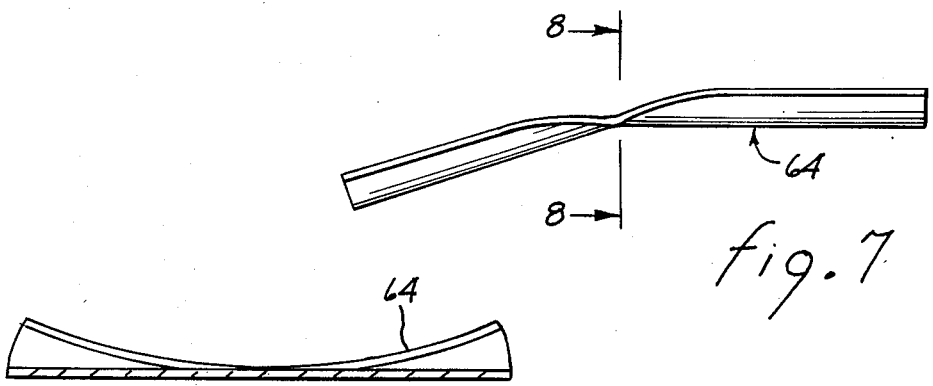
fig. 7
fig. 8
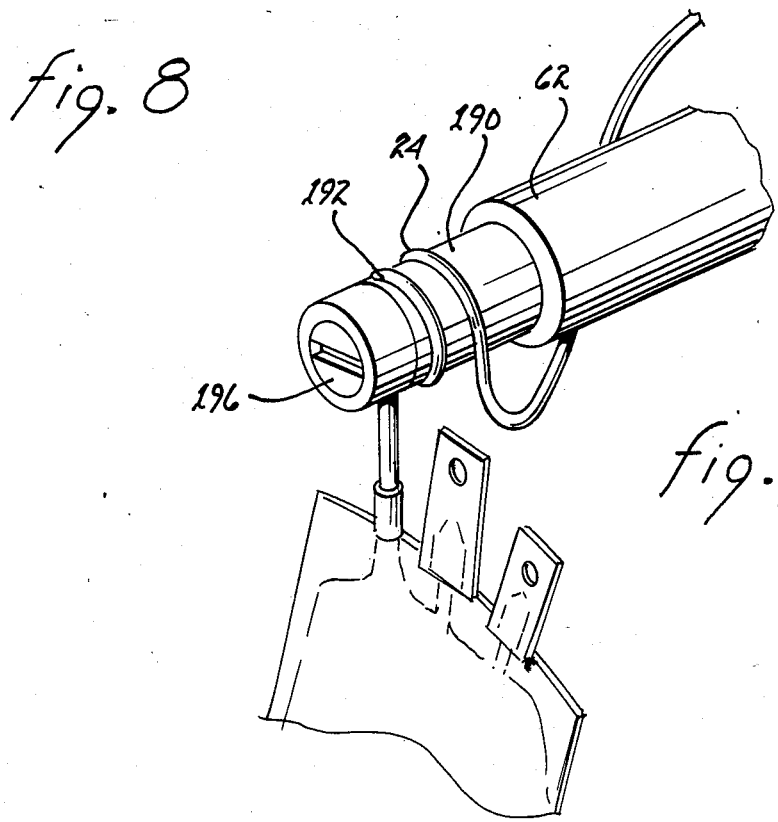
fig. 9

BLOOD COLLECTION BAG WEIGHT MONITOR

The present invention relates to weighing devices and, more particularly, to a two state device for regulating the final weight of a weight increasing element.

In private and public blood collection centers, whether for profit, for charity or in affiliation with a hospital, relatively crude techniques are employed to determine the degree of fill of each blood collection bag. In poorly funded blood collection centers, the degree of fill is monitored by one or more operators, which monitoring results in substantial diversity in the amount of blood in the collection bags. Such diversity or nonuniformity may result in penalties or strictures imposed by a monitoring federal agency for overfilled blood collection bags. Where payment by the blood collection center to the blood donors is made on a per blood collection bag basis, overpayment occurs when the blood collection bags are not filled to the norm.

Static weight monitoring apparatus have been employed which provide a visual indication, such as a scale, to an operator upon fill of a blood collection bag commensurate with a norm. Thereafter, further flow is terminated by the operator. Other apparatus which actuate mechanical, electrical or electro-mechanical elements on achievement of an approximated weight, have also been developed. One of the more sophisticated apparatus which employs dynamic, rather than static, weighing of the blood collection bag during fill is described in U.S. Pat. No. 4,027,735, which patent is assigned to the present assignee. The apparatus described therein continuously agitates the blood collection bag during fill to obtain good mixing with preservatives predisposed within the blood collection bag while simultaneously weighing the blood collection bag and terminating further flow thereinto on achievement of a predetermined weight.

Certain prior art apparatus which terminate the flow of blood into a filled collection bag in response to a signal generated by or as a result of the state of fill of the blood collection bag require a source of electrical power to actuate blood flow terminating equipment. This requirement limits the utility of the apparatus to locations where such electrical power is available or it must be transported along with the apparatus to the remote locations. Should the electrical power not be available in situ or through portable motor/generator sets, the operation of the blood collection center must be monitored solely by operators which monitoring results in nonuniformity in the fill of the blood collection bags, as described above.

To achieve uniformity of fill of blood collection bags and remove a dependency upon an in situ or transportable source of electrical power, the device described in U.S. Pat. No. 4,390,073, which patent is assigned to the present assignee, was developed. This device employs a blood collection bag weight responsive trigger to generate a very low energy electrical signal from a self-contained source of electrical power to release stored energy and perform the work required. Thereby, the device is readily fully self-contained and will accurately monitor and terminate the filling process of blood collection bags.

Due to poor initial funding or budgetary cutbacks, many blood collection centers do not have the funds necessary to purchase very accurate but relatively expensive weight monitors, such as described above. To meet the budgetary restraints imposed upon certain blood collection centers and yet provide a blood collection bag weight monitoring device of sufficient accuracy to prevent and avoid the various problems attendant under and overfilled bags, the device described herein was developed.

This device incorporates a trough configured spring interconnecting a fixed first part or element mountable upon a support stand and a movable second part or element from which is suspended a blood collection bag. The operational characteristics of a trough spring are such that it will remain essentially rigid until a deflection force imposed thereon exceeds a predetermined magnitude. Thereafter, a spring will abruptly flex and the two parts will become reoriented with respect to one another commensurate with the extent of permitted flex of the spring. By careful engineering of the moment arm defined between the spring and the point of suspension of the blood collection bag along with the flex parameter of the spring, the precise weight of the blood collection bag sufficient to cause the spring to flex is predeterminable. Upon flexing of the spring, a clamp mechanism is actuated by the resulting movement of the second element to clamp the fill tube to the blood collection bag and terminate further flow of blood thereinto.

It is therefore a primary object of the present invention to provide a completely mechanical device for terminating the flow of blood into a blood collection bag on achievement of a predetermined fill weight.

Another object of the present invention is to provide a blood collection monitoring device which employs a two state spring to terminate further flow of blood into a blood collection bag.

Yet another object of the present invention is to provide a two state monitoring device for limiting by weight the amount of flow of blood into a blood collection bag.

A further object of the present invention is to provide a force responsive two state spring for limiting by weight the amount of flow of blood into a blood collection bag.

A yet further object of the present invention is to provide a low cost accurate weight monitoring device for terminating the flow of blood into a blood collection bag.

A still further object of the present invention is to provide a self-contained monitoring device for terminating the flow of blood into a blood collection bag on achievement of a predetermined weight of fill.

These and other objects of the present invention will become apparent to those skilled in the art as the description thereof proceeds.

The present invention may be described with greater specificity and clarity with reference to the following drawings, in which:

FIG. 1 is a perspective view illustrating the present invention in operation;

FIG. 2 is a cross-sectional view taken along lines 2—2, as shown in FIG. 1;

FIG. 6 is a partial cross-sectional top view taken along lines 6—6, as shown in FIG. 3;

FIG. 7 illustrates the spring in its second state;

FIG. 8 is a cross-sectional view taken along lines 8—8, as shown in FIG. 7; and

FIG. 9 illustrates a variant of the blood collection bag supporting structure.

Figure 3:
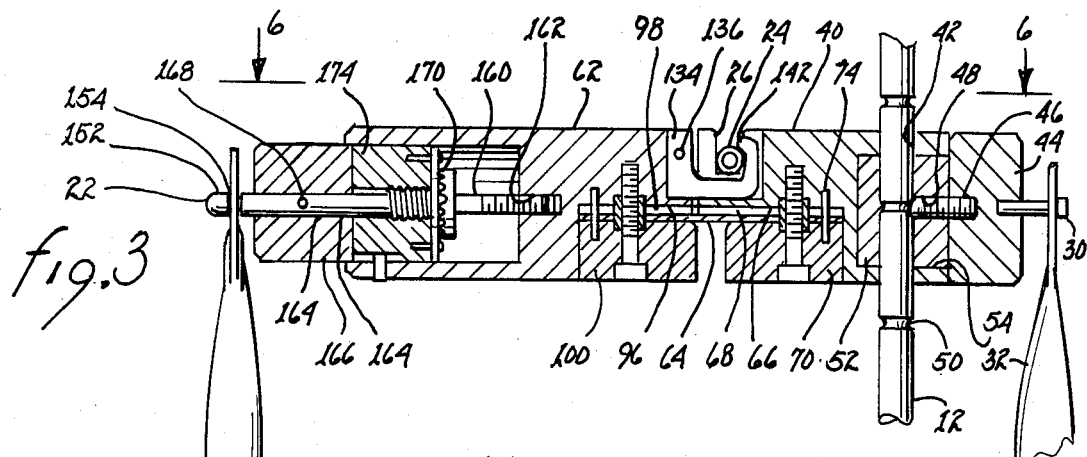
FIG. 3 is a cross-sectional view taken along lines 3—3, as shown in FIG. 2.

Referring to FIG. 1, there is shown a weight monitor 10 supported upon and extending from a post 12 anchored in a platform 14. The post and associated platform may be replaced by any other type of stand capable of supporting weight monitor 10 at an elevation sufficient to permit blood collection bag 16 depending therefrom to have a limited degree of unobstructed vertical movement. The blood collection bag is of a conventional and widely commercially available type. It includes a tab 18 having an aperture 20 disposed therein. The aperture is penetrably engaged by a pin 22 extending from the end of weight monitor 10. An integrally attached fill tube 24 extends from the blood collection bag and is routed through a slot 26. Within the slot are located selectively actuatable clamp means for clamping the fill tube to preclude further flow of blood therethrough. End 28 of the fill tube is in fluid communication with a vein of a blood donor during fill of blood collection bag 16. As shown in FIG. 3, a pin 30 may extend from the weight monitor to support a supplemental blood collection bag 32 related to the blood collection bag being filled.

The all mechanical weight monitor is capable of sustained heavy use and will withstand the rigors of mobile transportation from collection site to collection site without impairment or derogation of its high accuracy, which accuracy is on the order of plus or minus 3 grams per filled blood collection bag. Flow through the fill tube is automatically terminated when the blood collection bag, suspended from the weight monitor, achieves a predetermined weight. Upon such termination, the configuration of the weight monitor is automatically altered and provides a visual signal to an attendant. In the event termination is premature due to jostling of the blood collection bag or other reason, the weight monitor can be reset very easily to permit resumption of blood flow into the blood collection bag. Furthermore, calibration of the weight monitor is a simple matter of suspending therefrom a standardized weight; the calibration can readily be performed in the field or at a testing facility.

Figure 4:
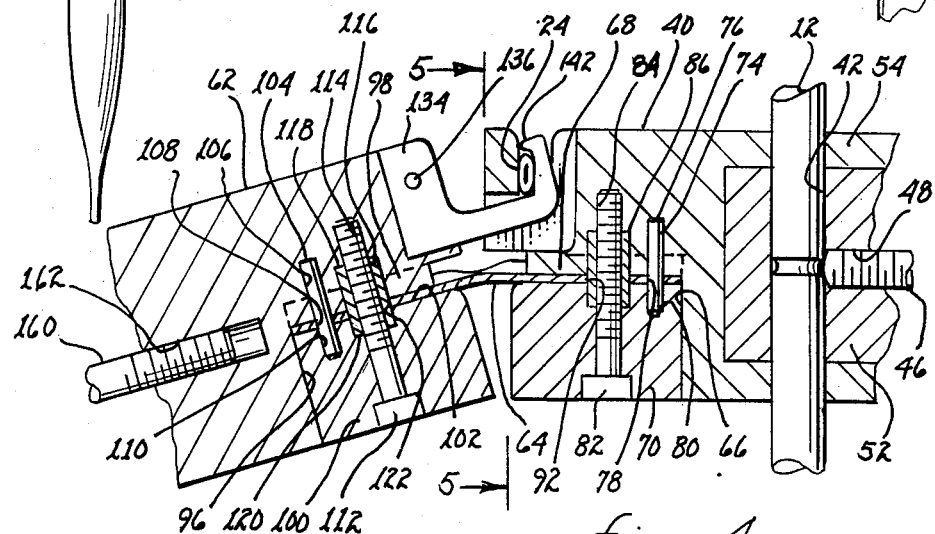
FIG. 4 is a cross-sectional detailed view of the spring in its second state.
Figure 5:
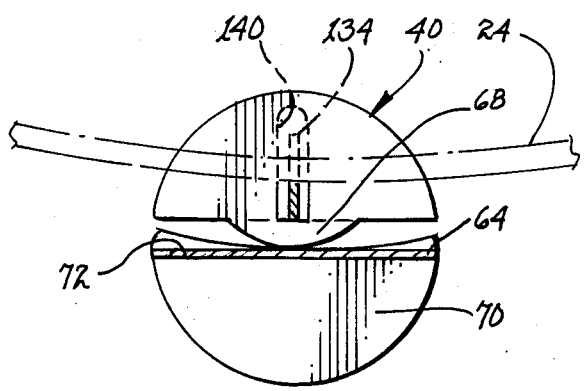
FIG. 5 is a cross-sectional view taken along lines 5—5, as shown in FIG. 4.

Referring jointly to FIGS. 1, 3 and 4, the mechanism for removably securing weight monitor 10 to post 12 will be described. Fixed end 40 of weight monitor 10 includes a passageway 42 extending transversely or diametrically therethrough for penetrably receiving post 12. Preferably, the cross-sectional configuration of the passageway is commensurate with the cross-section of the post to obtain a tight fit therebetween and provide a stable interconnection. Positional locking of the weight monitor to the post may be effected by rotation of clamping knob 44. This knob includes a threaded stud 46 threadedly engaging passageway 48 which intersects with passageway 42. The resulting interfering engagement between stud 46 and post 12 will lock the weight monitor at a predetermined elevation along the post. Such locking at predetermined elevations may be enhanced by forming within the post each of a plurality of spaced apart annular channels 50 for engagement with stud 46. For structural and/or manufacturing reasons, an insert 52 may be located within a shroud portion 54 of fixed end 40 by a retaining screw 56. Such insert includes passageways 42 and 48.

Referring jointly to FIGS. 1 to 6, weight monitor 10 will be described in detail. The weight monitor includes fixed end 40 and movable end 62 which is repositionable in either of two states. A spring 64 interconnects the fixed and movable ends and determines the positional state of the movable end. The spring is trough shaped in cross-section and may be rectangular in plan view. A force applied to such a spring in a radially outward direction will tend to cause essentially no deflection of the spring from a commensurate longitudinal line unless the applied force exceeds a predeterminable value. On application of such an excess force, the spring will "snap" or flex and then bend along a line essentially transverse to the longitudinal axis of the spring; see FIGS. 7 and 8. The cross-sectional configuration of the spring, at the point of flex, will change from an arc to an essentially straight line. Such cross-sectional transformation is believed to cause a slight and temporary elongation of the edges of the spring at the moment of near instantaneous flexing of the spring. It is believed that it is the elongation which accounts for the "snap" sound accompanying the near instantaneous flexing. The extend of ultimate bend of the spring subsequent to the initial flexing is a function of the force applied and the proximity of structures obstructing further bending. The flexing of the spring may be likened to a flat beam that is buckling in an elastic mode.

In order to accommodate accurate predeterminable flexing of the spring, it is preferable to secure opposing ends of the spring along a central longitudinal line of the spring, which line is of minimum width and wherein the securing elements intrude as little as possible upon the curvature of the spring lateral from the line of attachment. Pursuant to such preferred criteria, fixed end 40 includes a cutaway portion 66 having a section of a cylinder 68 centered therein and extending downwardly. A mating keeper 70 includes a planar surface 72 for contacting a longitudinal line of spring 64 and retaining the spring along a longitudinal line of cylinder 68. Since any skewing of the spring with respect to fixed end 40 may affect flex of the spring, a locating pin 74 extends from a cavity 76 in the fixed end through aperture 78 in spring 64 and into cavity 80 in keeper 70. Keeper 70 is retained adjacent spring 64 by a bolt 82 extending through keeper 70 into threaded cavity 84 in fixed end 40. To add stability and positional rigidity to spring 64, a sleeve 86 penetrably receives bolt 82 and is lodged within corresponding annular expansions in the fixed end and in the keeper and is in tight tolerance fit with aperture 92 in spring 64.

Movable end 62 includes a cutaway portion 96 having a section of a cylinder 98 centered therein and extending downwardly. A mating keeper 100 includes a planar surface 102 contacting a longitudinal line of spring 64, which line is an extension of that in contact with keeper 70. To prevent any skewing of movable end 62 with respect to spring 64, a locating pin 104 extends from a cavity 106 within the movable end through aperture 108 in spring 64 and into cavity 110 in keeper 100. Keeper 100 is retained by threaded bolt 112 extending therefrom into threaded cavity 114 within movable end 62. To aid the positional rigidity of spring 64 with respect to the movable end, a sleeve 116 circumscribes the shank of bolt 112 and snuggly mates with annular expansions 118, 120 in the movable end and the keeper, respectively, and through an aperture 122 in spring 64.

As may be noted from the figures, keepers 70 and 100 are displaced from one another along the axis of the weight monitor. The extent of space therebetween must be, at the minimum, adequate to permit angular repositioning of the movable end with respect to the first end upon application of a force thereto sufficient to cause spring 64 to flex. To prevent damage to the spring due to overbending at the point of flexure, constraints with respect to further repositioning of the fixed and movable ends are preferred; the clamping of the fill tube creates restraint against further repositioning. Alternatively, as illustrated in FIG. 4, such constraints may be by purposely providing an interfering relationship between the two keepers upon a predetermined angular excursion between the fixed and movable ends.

The means for clamping the fill tube upon achievement of the predetermined fill weight of the blood collection bag will be described with reference to FIGS. 1, 3, 4 and 6. Fixed end 40 includes transverse slot 26 disposed in the upper portion thereof. This slot is preferably of a width approximately equal to the diameter of fill tube 24. A hook 134 is pinned or otherwise secured to movable end 62 by pin 136. The hook extends from within a slot 138 in movable end 62 into a correspondingly oriented slot 140 disposed in fixed end 40. Hook 134 includes a nubble 142, which nubble extends into slot 26. The dimension of the nubble is selected to preclude insertion and removal of tubing 24 from within slot 26 without requiring partial compression of the tubing. Thereby, the nubble serves in the mannner of a retaining element to prevent inadvertent removal of the tubing from within the slot.

Upon flexing of spring 64, movable end 62 will become reoriented with respect to the fixed end. Such reorientation will cause hook 134 to be angularly repositioned with respect to the fixed end to bring the hook into slot 26 and compress tubing 24 between a wall of the slot and the hook. The compressed tubing will inhibit further fluid flow therethrough and further filling of the attached blood collection bag will be terminated.

The weight monitor can be reset by manually raising movable end 62 into aligned relationship with fixed end 40 if repositioning was inadvertent. After a filled blood collection bag is disengaged from pin 22, the movable end will usually reposition itself due to the force exerted by the spring; alternatively, it can be reset manually.

The blood collection bag to be filled is suspended from pin 22 located at the end of movable end 62. The pin may include a knob 152 defining an annular groove 154 for receiving apertured tab 18 of blood collection bag 16. The force required to flex spring 64 is a function of the weight imposed times the moment arm through which the weight acts. To permit a certain variation in weight and/or, to accommodate for different flex parameters of spring 64 as well as for age and deterioration, the moment arm represented by movable end 62 is adjustable.

A threaded shank 160 is in threaded engagement with threaded cavity 162 within movable end 62. Shank 164, interconnecting threaded shank 160 and pin 22, supports adjustment knob 166 and is rotatably locked therewith through pin 168 penetrably lodged in aligned passageways within the knob and shank 164. Accordingly, rotation of adjustment knob 166 will cause threaded shank 160 and pin 22 to translate longitudinally with respect to movable end 62.

Figure 10:
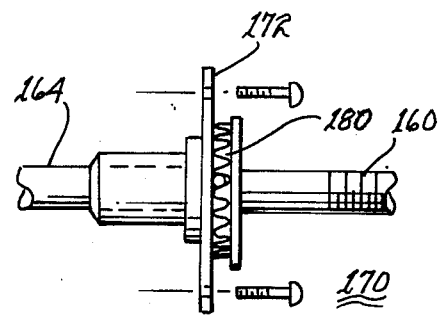
FIG. 10 illustrates a detent assembly.

To provide micrometer-like adjustments, a detent assembly shown particularly in FIGS. 3, 6 and 10 and generally identified by numberal 170, may be employed. The detent assembly includes a plate 172 affixed to detent mount 174. The detent mount includes a longitudinally oriented slot 176 for receiving a retaining screw 178 extending thereinto from the shroud portion of movable end 62 for enclosing the detent mount. Thereby, rotation of the detent mount is precluded. The detent assembly includes spring and ball means 180 to provide a plurality of step-like functions for each revolution of adjustment knob 166. Thereby, very precise positioning of pin 22 along the longitudinal axis of movable end 62 can be effected. Such precise positioning of the pin controls the moment arm through which the weight of the blood collection bag acts. Highly accurate control of the fill weight of the blood collection bag is therefore possible through accurate dimensioning of the moment arm commensurate with the force necessary to flex spring 64.

As illustrated in FIG. 9, the fill tube itself may be employed to suspend the blood collection bag 16 from the movable end. A longitudinally positionable plunger 190 includes a helical groove 192 for receiving and frictionally retaining approximately one and a half wraps of fill tube 24. The longitudinal location of the plunger can be controlled by a threaded shaft threadedly engaging a threaded cavity within the movable end. A slotted knob 196 for rotating the shaft may be employed to facilitate rotation. Thereby, rotation of knob 196 will regulate the longitudinal position of plunger 190 to establish the moment arm through which the weight of blood collection bag 16 is to act.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

We claim:

1. A weight monitor for monitoring the fill of a blood collection bag, said weight monitor comprising in combination:
   (a) a fixed end;
   (b) a movable end;
   (c) means for suspending the blood collection bag from said movable end; and
   (d) spring means for interconnecting said fixed end with said movable end and for repositioning said movable end from a first state to a second state on application upon said movable end of a predetermined force presented by the weight of a filled blood collection bag, said spring means having the characteristic of a buckling beam to abruptly reposition said movable end with a snap action upon application of the predetermined force and to essentially resist repositioning of said movable end in response to any applied force of a lesser magnitude than the predetermined force.

2. The weight monitor as set forth in claim 1 wherein the blood collection bag includes a fill tube and wherein said weight monitor includes clamp means for terminating flow through the fill tube.

3. The weight monitor as set forth in claim 2 including means for actuating said clamp means coincident with repositioning of said movable end from the first state to the second state.

4. The weight monitor as set forth in claim 3 wherein one operative element of said clamp means is disposed in said movable end and another operative element of said clamp means is disposed in said fixed end.

5. The weight monitor as set forth in claim 4 wherein said one element comprises a hook and wherein said other element comprises a sidewall.

6. The weight monitor as set forth in claim 5 including means for restraining inadvertent disengagement of the fill tube from said clamp means prior to repositioning of said movable end to the second state.

7. The weight monitor as set forth in claim 6 wherein said restraining means comprises a nubble located upon said hook.

8. The weight monitor as set forth in claim 1 wherein said spring means is characterized as subject to buckling in an elastic mode upon application of a bending force greater than a predetermined magnitude.

9. The weight monitor as set forth in claim 1 wherein said weight monitor is devoid of any electrically actuated elements.

10. The weight monitor as set forth in claim 1 including means for relocating said suspension means to alter the moment arm through which the weight of the blood collection bag acts.

11. The weight monitor as set forth in claim 10 wherein said relocating means comprises a threaded shaft in threaded engagement with a cavity disposed in and longitudinally aligned with said movable end.

12. The weight monitor as set forth in claim 1 including means for supporting said fixed end at a height sufficient to suspend freely the blood collection bag from said movable end.

13. A weight monitor for monitoring the fill of a blood collection bag, said weight monitor comprising in combination:
(a) a fixed end;
(b) a movable end;
(c) means for suspending the blood collection bag from said movable end; and
(d) spring means for interconnecting said fixed end with said movable end and for repositioning said movable end from a first state to a second state on application upon said movable end of a predetermined force presented by the weight of a filled blood collection bag, said spring means comprising a trough shaped spring having a concave surface and a convex surface when said movable end is in the first state.

14. The weight montior as set forth in claim 13 wherein said fixed end includes means for retaining one end of said spring and wherein said movable end includes further means for retaining the other end of said spring.

15. The weight monitor as set forth in claim 14 wherein each of said retaining means and said further retaining means includes a cylindrical section for contacting longitudinally the concave surface and a keeper for contacting longitudinally the convex surface in opposing relationship to said cylindrical section.

16. The weight monitor as set forth in claim 15 including means for anchoring said spring with both said fixed end and said movable end to prevent skewing of said spring relative to said fixed end and said movable end.

17. The weight monitor as set forth in claim 16 wherein said anchoring means includes pins extending through said spring.

18. A weight monitor for terminating the flow of blood through a fill tube into a blood collection bag on fill to a predetermined weight, said weight monitor comprising in combination:
(a) a fixed end;
(b) a movable end for suspending the blood collection bag;
(c) spring means interconnecting said fixed end and said movable end for repositioning said movable end from a first state to a second state in response to a force related to a predetermined fill weight of the blood collection bag and exerted upon said movable end by the blood collection bag said spring means being characterized as essentially inflexible to maintain said movable end essentially immobile in response to application of a bending force of a magnitude less than a predetermined force and as subject to buckling in an elastic mode only upon application of a bending force equal to or of a magnitude greater than the predetermined force;
(d) means for altering the magnitude of the force exerted upon said spring means by the predetermined fill weight; and
(e) means for terminating flow through the fill tube coincident with the change of state of said movable end.

19. The weight monitor as set forth in claim 18 wherein said terminating means includes means for clamping the fill tube.

20. The weight monitor as set forth in claim 18 including means for supporting said fixed end at a height sufficient to suspend the blood collection bag from said movable end.

21. A weight monitor for terminating the flow of blood through a fill tube into a blood collection bag on fill to a predetermined weight, said weight monitor comprising in combination:
(a) a fixed end;
(b) a movable end for suspending the blood collection bag;
(c) spring means interconnecting said fixed end and said movable end for repositioning said movable end from a first state to a second state in response to a force related to a predetermined fill weight of the blood collection bag and exerted upon said movable end by the blood collection bag, said spring means including a longitudinal axis extending from said fixed end to said movable end and a concave upwardly opening cross-section transverse to the longitudinal axis;
(d) means for altering the force exerted upon said spring means by the predetermined fill weight; and
(e) means for terminating flow through the fill tube coincident with the change of state of said movable end.

22. A weight monitor for terminating the flow of blood through a fill tube into a blood collection bag on fill to a predetermined weight, said weight monitor comprising in combination:
(a) a fixed end;
(b) a movable end for suspending the blood collection bag;
(c) spring means interconnecting said fixed end and said movable end for repositioning said movable end from a first state to a second state in response to a force related to a predetermined fill weight of the blood collection bag and exerted upon said movable end by the blood collection bag;

(d) means for altering the force exerted upon said spring means by the predetermined fill weight, said altering means including means for adjusting the distance along said movable end between said spring means and the suspended blood collection bag; and (e) means for terminating flow through the fill tube coincident with the change of state of said movable end.

* * * * *